(12) United States Patent
Auderset et al.

(10) Patent No.: US 8,092,218 B2
(45) Date of Patent: Jan. 10, 2012

(54) ARRANGEMENT FOR FASTENING A DENTAL PROSTHESIS TO A MALE BAR

(75) Inventors: Adrian Auderset, Nidau (CH); Mathias Strazza, Nidau (CH); Jean-Fred Studer, Lamboing (CH); Hans Messerli, Biel/Bienne (CH)

(73) Assignee: Cendres & Metaux SA, Biel/Bienne (CH)

( * ) Notice: Subject to any disclaimer, the term of this patent is extended or adjusted under 35 U.S.C. 154(b) by 446 days.

(21) Appl. No.: 11/812,494

(22) Filed: Jun. 19, 2007

(65) Prior Publication Data
US 2007/0298655 A1 Dec. 27, 2007

(30) Foreign Application Priority Data
Jun. 21, 2006 (EP) .................................. 06405265

(51) Int. Cl.
*A61C 13/12* (2006.01)
*A61C 13/225* (2006.01)

(52) U.S. Cl. ...................................... 433/172

(58) Field of Classification Search .................. 433/172, 433/176, 177, 180, 181, 182, 183, 173
See application file for complete search history.

(56) References Cited

U.S. PATENT DOCUMENTS

| 1,367,885 | A | | 2/1921 | Means |
| 5,567,155 | A | * | 10/1996 | Hansen ....................... 433/172 |
| 6,332,364 | B1 | * | 12/2001 | Buschmann et al. ........... 73/788 |
| 7,172,422 | B1 | * | 2/2007 | Essiger ....................... 433/173 |
| 2002/0039719 | A1 | * | 4/2002 | Honkura et al. ............. 433/189 |
| 2004/0005530 | A1 | * | 1/2004 | Mullaly et al. ............... 433/172 |

FOREIGN PATENT DOCUMENTS

| DE | 29 45 489 A1 | 11/1979 |
| EP | 0 473 933 A1 | 3/1992 |

* cited by examiner

*Primary Examiner* — Cris L Rodriguez
*Assistant Examiner* — Eric Rosen
(74) *Attorney, Agent, or Firm* — Foley & Lardner LLP

(57) ABSTRACT

The arrangement for fastening a dental prosthesis to a male bar including a female housing that is connectable to the dental prosthesis and at least two inserts that are insertable into the female housing and extend over the male bar when the female housing is attached to the latter. The arrangement allows a simpler adjustment of the retention force that retains the female housing on the male bar.

18 Claims, 10 Drawing Sheets

ARRANGEMENT FOR FASTENING A DENTAL PROSTHESIS TO A MALE BAR

This Application claims benefit under 35 U.S.C. §119(e) of Europe Application Number 06405265.7, filed Jun. 21, 2006, the disclosure of which is incorporated by reference herein.

FIELD OF THE INVENTION

The present invention relates to an arrangement for fastening a dental prosthesis to a male bar, the arrangement comprising a female housing that is connectable to the dental prosthesis.

BACKGROUND OF THE INVENTION

Such an arrangement is known from DE 29 45 489 A1. For a force-fitting connection of the female housing to the male bar, a rubber-elastic material is provided which is embedded in two longitudinal grooves of the female housing. The shape and size of the rubber-elastic material are predetermined. If, in order to be fastened to the dental prosthesis, the female housing has to be shortened due to the geometrical situation, the retention force that retains the female housing on the male part will be changed. In this arrangement, no adjusting capability of this retention force is provided.

From EP 473 933 A1, a connection to a male bar is known which an elastic spring member is attached to. Here also, the shape and size of the spring member are predetermined so that a subsequent adjustment of the retention force is not possible.

Furthermore, arrangements that are intended for model casting are available on the market which include a selection of different plastic inserts acting upon the bar with various degrees of friction. When casting a prosthesis framework, there is provided a recess for the plastic insert that is to be subsequently inserted into the cast prosthesis framework. These arrangements suffer from the disadvantage that each casting has to be performed individually and the manufacture is therefore relatively laborious and expensive. Furthermore, the inserted plastic insert defines the retention force. If the latter is to be changed, the plastic insert has to be replaced with another one. A subsequent adjustment of the retention force is therefore only possible to a limited extent.

SUMMARY OF THE INVENTION

On the background of this prior art, it is an object of the present invention to provide an arrangement that allows the fastening of a dental prosthesis to a male bar and adjusting the retention force by which the female housing is retained on the male bar in a simpler manner.

This is accomplished by an arrangement comprising a female housing that is connectable to the dental prosthesis, and at least two inserts for adjusting the retention force retaining the female housing on the male bar. The two inserts are insertable into the female housing and extend over said male bar when the female housing is attached to said male bar.

The retention force can be adjusted in a simple manner by selectively inserting a number of inserts into the female housing.

BRIEF DESCRIPTION OF THE DRAWINGS

The invention will be explained in more detail hereinafter with reference to drawings of exemplary embodiments, where.

DETAILED DESCRIPTION OF THE PREFERRED EMBODIMENT

First Exemplary Embodiment

FIGS. 1 to 5 show different views of female housing 10 that is e.g. fastened to a dental prosthesis by means of a polymerizate and attachable to a bar-shaped male part.

Figures 1, 2, 3:
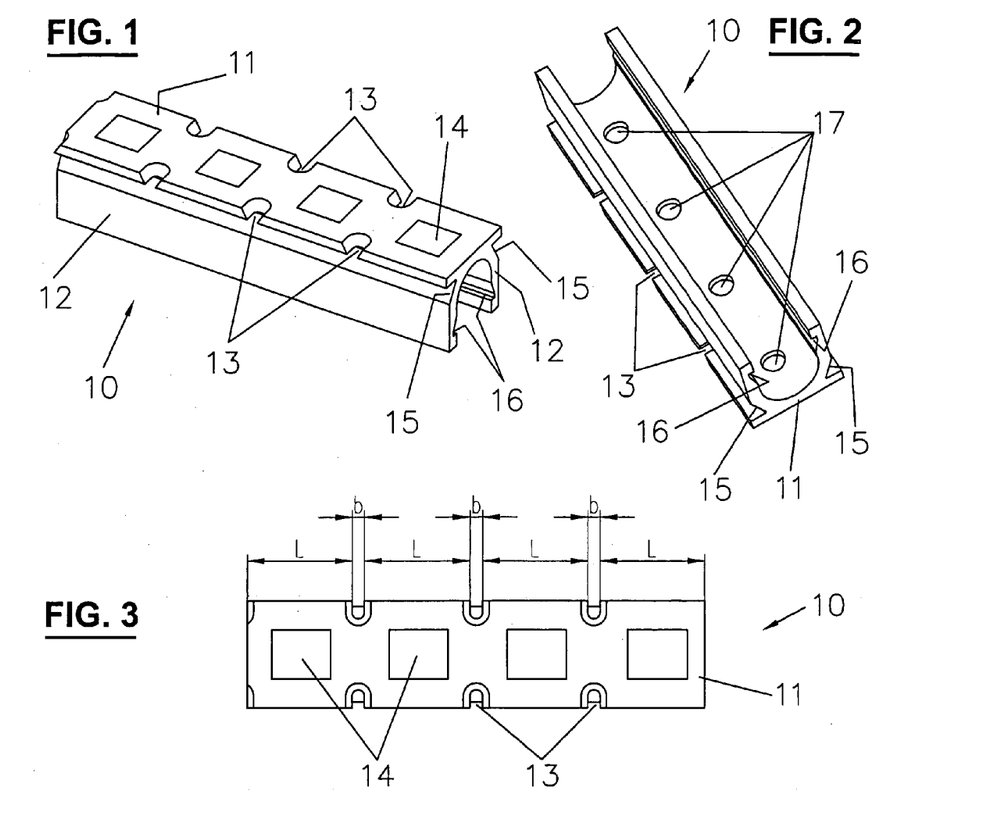
FIG. 1 shows a first exemplary embodiment of the female housing of an arrangement according to the invention in a perspective view from above.
FIG. 2 shows the female housing of FIG. 1 in a perspective view from below.
FIG. 3 shows the female housing of FIG. 1 in a top view.
Figure 4:
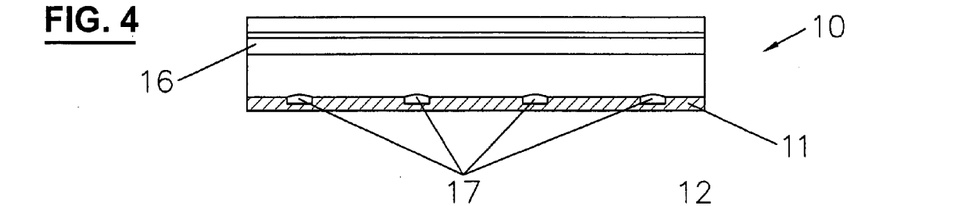
FIG. 4 shows the female housing of FIG. 1 in a sectioned side view according to line IV-IV in FIG. 5.
Figure 5:
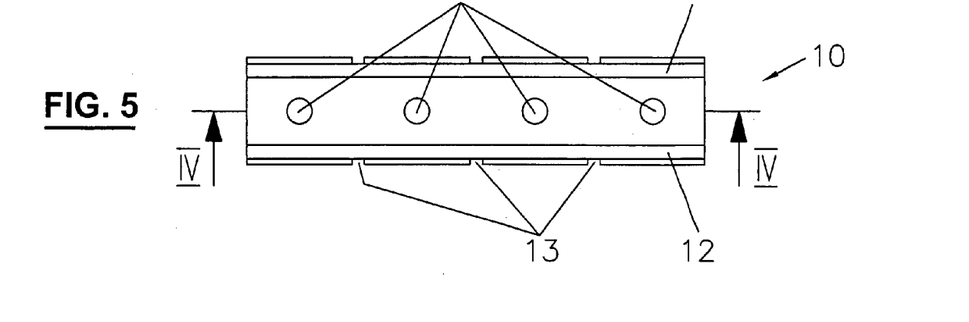
FIG. 5 shows the female housing of FIG. 1 in a bottom view.

Female housing 10 comprises a basic housing element having a predetermined length L that is e.g. smaller than 10 mm or smaller than 5 mm and is e.g. equal to 3.5 mm. Female housing 10 includes a number of adjoining basic housing elements and thus forms a straight, one-piece bar rider. The total length of female housing 10 is adjustable by cutting off a section e.g. by means of a cutting-off wheel.

Female housing 10, particularly the basic housing element, comprises a cover plate 11 provided with two side walls 12. The two side walls 12 are shaped essentially mirror-symmetrically.

Cover plate 11 is provided at regular spaces with marks in the form of incisions 13 situated on the two longitudinal edges of cover plate 11. Incisions 13 define the possible positions where female housing 10 can be shortened and are shaped such as to guide the cutting-off wheel while female housing 10 is being shortened. Each incision 13 has a width b that is chosen such as to take into account the cuttings that are produced when female housing 10 is shortened. Width b corresponds to the thickness of the cutting-off wheel, for example. The total length of female housing 10 is thus equal to $N*L+(N-1)*b$, where N is the number of basic housing elements (see FIG. 3). As appears in FIGS. 1 and 3, incisions 13 are limited by an edge that tapers from the upper side of cover plate 11 toward its underside.

Instead of incisions 13 or in addition to the incisions, the individual basic housing elements may be marked by grooves.

Optionally, engravings 14 may be provided which are applied at substantially regular spaces to female housing 10, e.g. on the external and/or internal side of cover plate 11. In FIGS. 1 and 3, engravings 14 are indicated merely symbolically by rectangles. They may take any desired form, e.g. that of a logo, of symbols, inscriptions, etc., and are applied by usual methods, more particularly engraving by means of milling or a laser. Engravings 14 serve as a carrier of certain information, e.g. on the provenance of the product and/or its designation.

The area where the respective side wall 12 connects to cover plate 11 is provided with a retaining groove 15. Therefore, the longitudinal edges of cover plate 11 project a little from side walls 12, thereby ensuring that female housing 10 is firmly retained when embedded in the dental prosthesis.

The inner side of each side wall 12 is provided with a longitudinal groove 16. Each basic housing element has a recess 17 on the inside of cover plate 11.

Each basic housing element of female housing 10 forms a location for receiving an insert 20. FIGS. 6 to 9 show different illustrations of such an insert 20.

Figure 6:
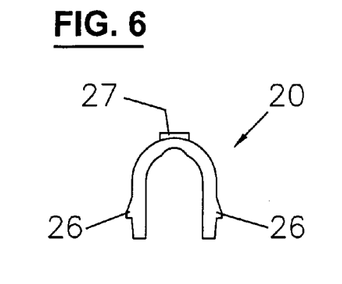
FIG. 6 shows a first exemplary embodiment of an insert of an arrangement according to the invention in a front view.
Figure 7:
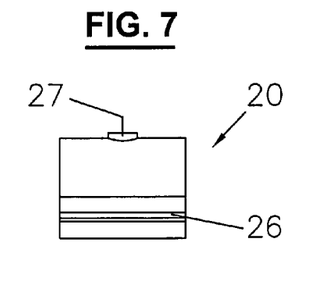
FIG. 7 shows the insert of FIG. 6 in a side view.
Figure 8:
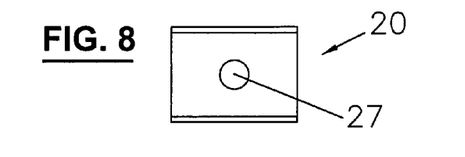
FIG. 8 shows the insert of FIG. 6 in a top view.
Figure 9:
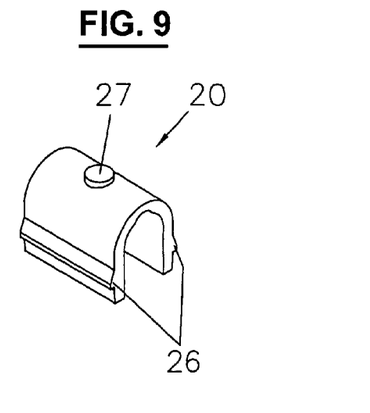
FIG. 9 shows the insert of FIG. 6 in a perspective view.

As appears particularly in FIG. 6, insert 20 has a substantially U-shaped cross-section. The external side of insert 20 is essentially complementary to the internal side of the basic housing element. More specifically, the external sides of insert 20 each have a stepped configuration, thereby forming a longitudinal wing 26. On the occlusal side of insert 20, a projection 27 is provided. When insert 20 is inserted into one of the basic housing elements, longitudinal wings 26 will engage in longitudinal grooves 16 of female housing 10 and projection 27 will engage in recess 17.

The shape of longitudinal grooves 16 and of longitudinal wings 26 is chosen such that insert 20 is firmly held inside female housing 10 particularly when the female housing, particularly the dental prosthesis, is withdrawn from the male bar in the withdrawal direction.

Figures 10, 11:
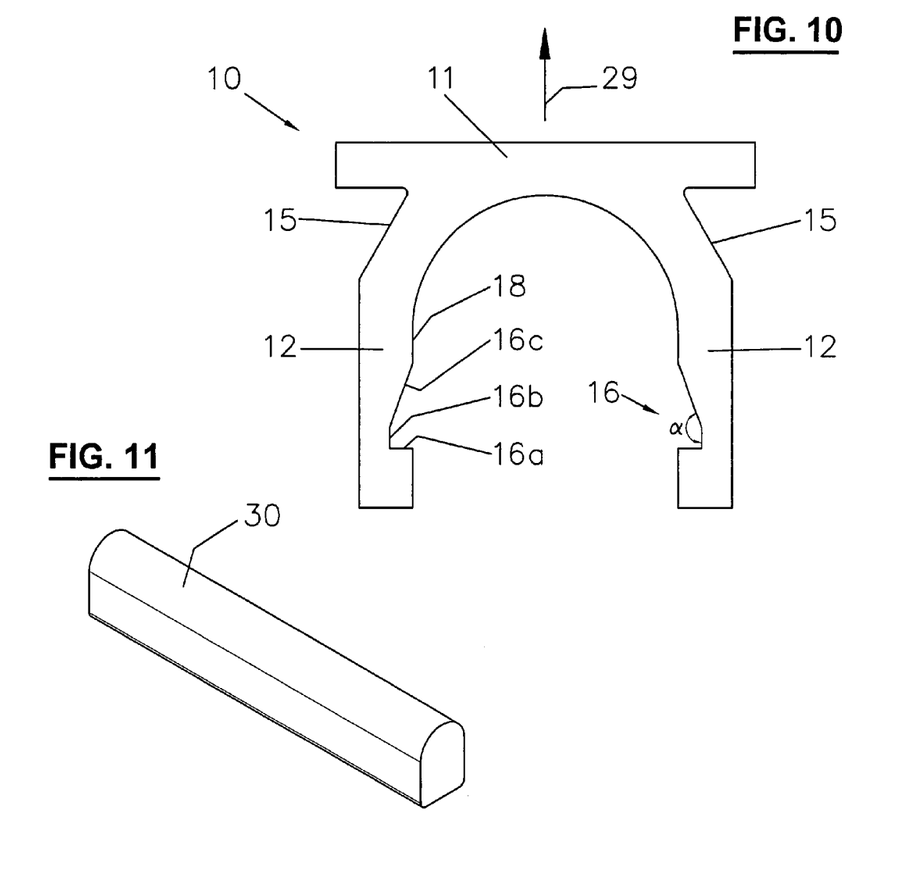
FIG. 10 shows the female housing of FIG. 1 in a front view.
FIG. 11 shows a perspective view of a male bar for receiving the female housing of FIG. 1 provided with inserts according to FIG. 6.

In FIG. 10, which shows a front view of female housing 10 in a greatly enlarged illustration, the withdrawal direction is indicated by arrow 29. The cross-section of each longitudinal groove 16 comprises a first section 16a that is essentially perpendicular to withdrawal direction 29 and adjoins to a second section 16b. The latter is closer to cover plate 11, i.e. to the occlusal side of female housing 10 than first section 16a. Second section 16b is essentially parallel to withdrawal direction 29 and adjoins to a third section 16c of longitudinal groove 16. The angle α between second section 16b and third section 16c is greater than 90 degrees and smaller than 180 degrees. The angle α is preferably comprised in the range of 125 degrees to 170 degrees. Third section 16c is followed by a fourth section 18 that adjoins to the U shape of the inner surface of female housing 10. Sections 16a, 16b, and 16c are substantially straight.

Side wall 12 has its thinnest part in the area of second section 16*b*. The distance between this section 16*b* and the basal end of female housing 10 is kept as small as possible in order to minimize the lever arm acting on the thinnest part when female housing 10 is under load. In addition, the selected shape of longitudinal groove 16 ensures that the thinnest part of side wall 12 gradually connects to the thicker wall in fourth section 18 and is thus solidly connected to the remainder of female housing 10. Tests have shown that female housing 10 also resists high loads without the occurrence of a rupture. It has further been found that a female housing whose longitudinal grooves have a rectangular or semicircular cross-section is less resistant and that the side wall may break off.

FIG. 11 shows male bar 30 to which female housing 10 provided with inserts 20 is attachable. As appears in FIG. 14 also, male bar 30 has a U-shaped cross-section and its two side surfaces are parallel to each other. Such a male bar is also known as the Dolder bar. Female housing 10 and insert 20 are so designed that they are also applicable with already existing male bars.

Figure 12:
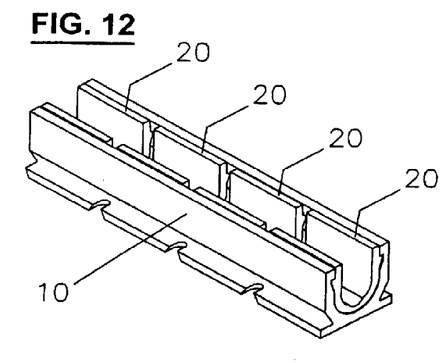
FIG. 12 shows the female housing of FIG. 1 with four inserts according to FIG. 6 inserted therein in a perspective view from below.
Figure 13:
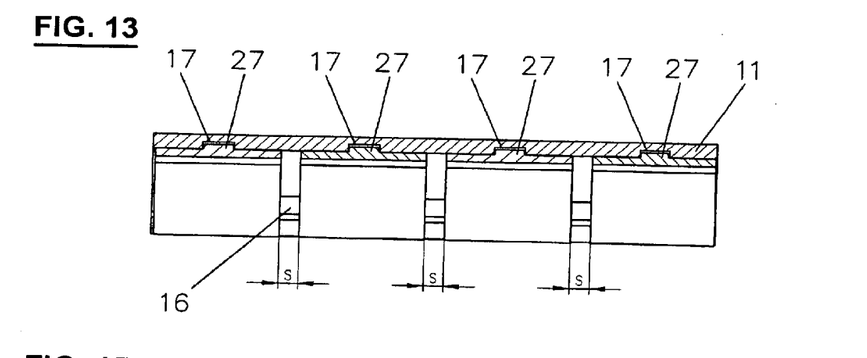
FIG. 13 shows the arrangement of FIG. 12 in a sectioned side view according to line XIII-XIII in FIG. 14, the male bar not being shown.

FIGS. 12 and 13 show a female housing 10 with four inserts 20 inserted therein. The projection 27 of each insert 20 engages in a recess 17 of the respective basic housing element. Projection 27 and recess 17 thus form positioning means which determine the position of each insert 20 in female housing 10. When inserted in female housing 10, positioning means 17, 27 prevent the inserts 20 from being displaced along female housing 10.

Figure 14:
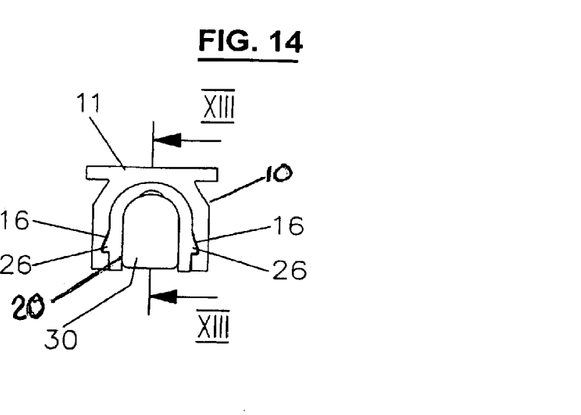
FIG. 14 shows a front view of the arrangement of FIG. 12 attached to a male bar according to FIG. 11.

As shown in FIG. 14, insert 20 is arranged between female housing 10 and male bar 30. Insert 20 is closed on the occlusal side so as to extend over male bar 30.

The length of insert 20 essentially corresponds to the length L of the basic housing element. Therefore, between two inserts 20 that are inserted in female housing 10 adjacent one another, a gap s results that essentially corresponds to the width b.

Hereinafter, the force that retains female housing 10 on bar 30 will be called "retention force". The force that is required in order to withdraw female housing 10 from bar 30 is called "withdrawal force". The withdrawal force and the retention force are equal in magnitude but act in opposite directions.

Figure 15:
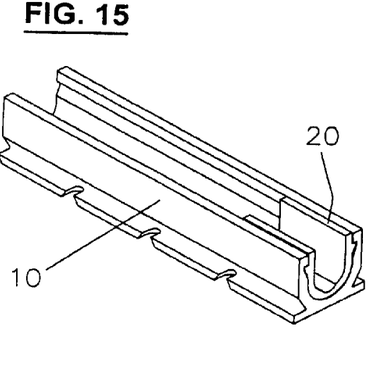
FIG. 15 shows the female housing of FIG. 1 with an insert according to FIG. 6 inserted therein in a perspective view from below.
Figure 16:
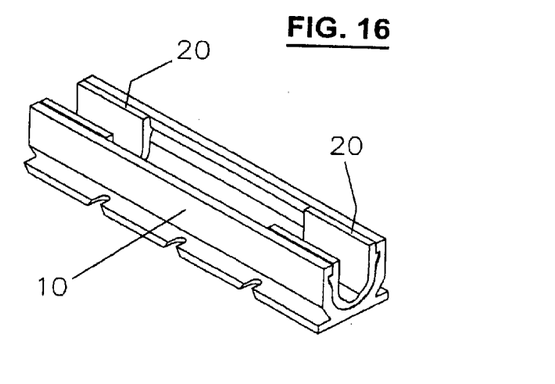
FIG. 16 shows the female housing of FIG. 1 with two inserts according to FIG. 6 inserted therein in a perspective view from below.

In the here depicted example, female housing 10 attached to male bar 30 is primarily retained by the friction acting between inserts 20 and male bar 30. The friction and thus the retention force and the withdrawal force can be adjusted in a simple manner by the choice of the number of inserts 20 that are inserted and of the positions in which they are inserted. In the example according to FIG. 15, only one insert 20 is inserted in the outermost basic housing element. In the example according to FIG. 16, a respective insert 20 is mounted in the two outer basic housing elements.

Optionally, inserts 20 of different kinds may be provided which differ e.g. in thickness, thereby resulting in further possibilities for adjusting the retention force and the withdrawal force.

Female housing 10 as well as inserts 20 are prefabricated and include or consist of an orally resistant material, e.g. a suitable metal such as titanium or a synthetic material such as polyetheretherketone (PEEK) or polyoxymethylene (POM).

Inserts 20 are made elastic so as to be insertable into female housing 10. They need not be made of plastic material exclusively but may alternatively comprise a metal framework that is coated with a plastic material.

Figures 17, 18, 19, 20, 21:
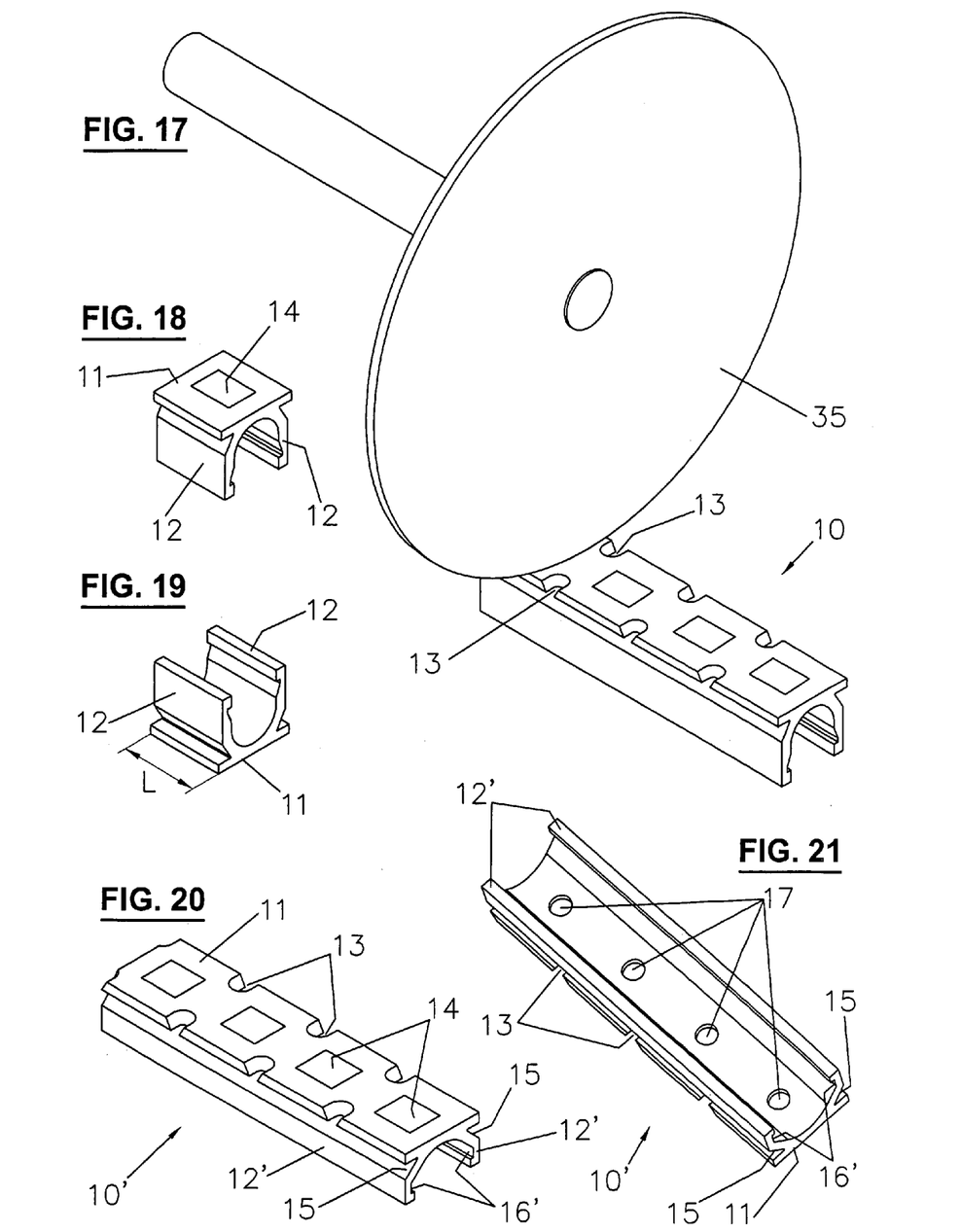
FIG. 17 shows the female housing of FIG. 1 together with a cut-off wheel in a perspective view.
FIG. 18 shows the basic housing element of the female housing of FIG. 1 in a perspective view from above.
FIG. 19 shows the basic housing element of FIG. 18 in a perspective view from below.
FIG. 20 shows a second exemplary embodiment of the female housing of an arrangement according to the invention in a perspective view from above.
FIG. 21 shows the female housing of FIG. 20 in a perspective view from below.
Figure 22:
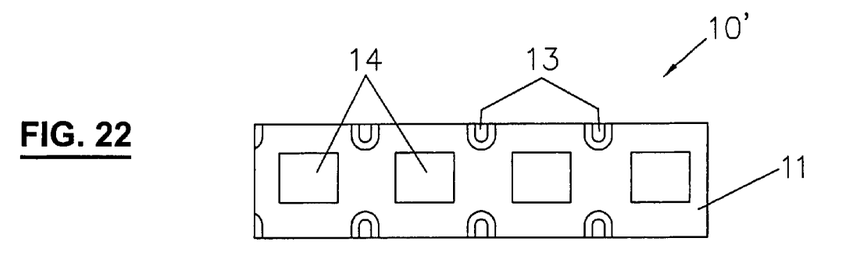
FIG. 22 shows the female housing of FIG. 20 in a top view.
Figure 23:
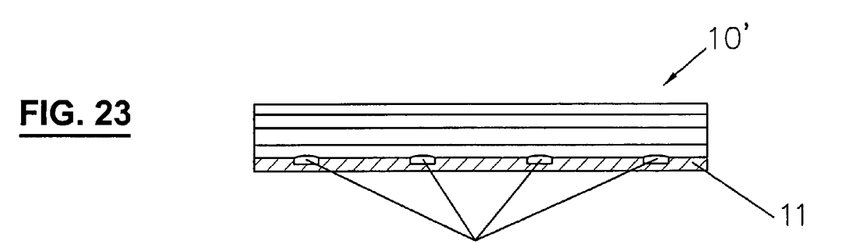
FIG. 23 shows the female housing of FIG. 20 in a sectioned side view according to line XXIII-XXXIII in FIG. 24.
Figure 24:
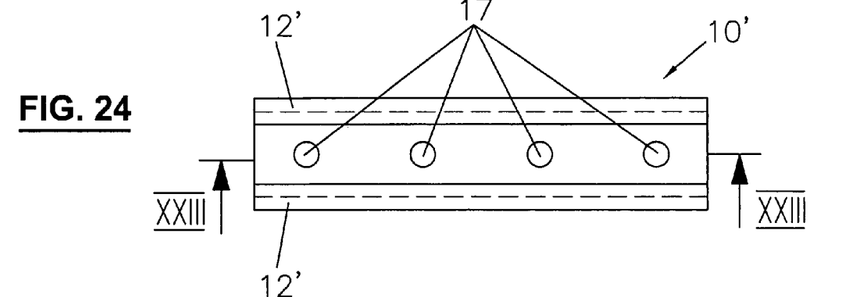
FIG. 24 shows the female housing of FIG. 20 in a bottom view.

Female housing 10 is produced as a long profile bar from which the user may cut off a female housing 10 of the desired length. For this purpose, a usual cutting-off wheel 35 as it is shown in FIG. 17 can be used. During the cutting operation, cutting-off wheel 35 is guided by incisions 13. It is possible to insert respective inserts 20 in the two basic housing elements adjoining the intended separating line before the cutting operation. The two front surfaces of inserts 20 will thus form additional guiding surfaces for cutting-off wheel 35. It is also possible to provide two separate auxiliary parts that are inserted into the two basic housing elements, the auxiliary parts having the same exterior surfaces as insert 20 but consisting of another material, e.g. a harder one.

It is further conceivable to produce a long profile bar having the external shape of insert 20 and from which the user may cut off individual inserts 20.

In addition to the long female housing 10, female housings that are manufactured as individual basic housing elements may further be provided, see FIGS. 18 and 19. The latter need no longer be separated and can be fastened in the prosthesis directly.

Second Exemplary Embodiment

FIGS. 20 to 24 show a second exemplary embodiment of female housing 10' and FIGS. 25 to 28 show the appropriate insert 20'. Parts that correspond to the parts of the first exemplary embodiment are designated by the same reference numerals.

Figures 29, 30:
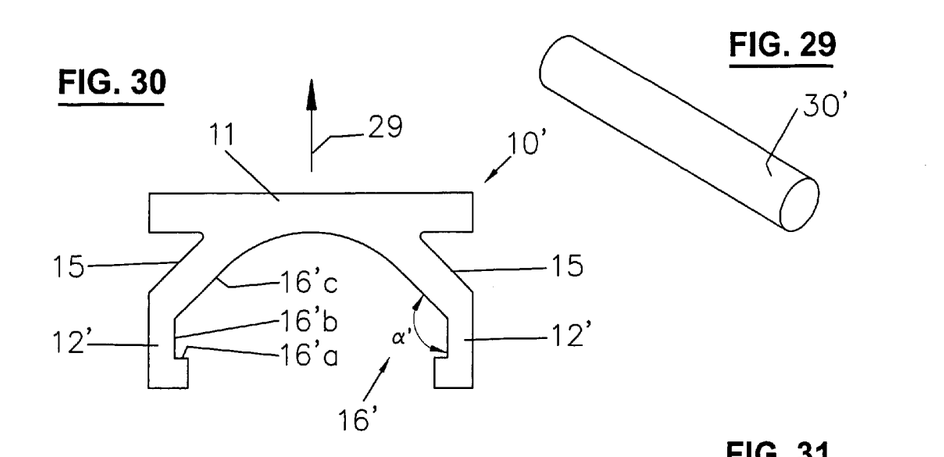
FIG. 29 shows a perspective view of a male bar for receiving the female housing of FIG. 20 provided with inserts according to FIG. 25.
FIG. 30 shows the female housing of FIG. 20 in a front view.

The second exemplary embodiment essentially differs from the first exemplary embodiment in that female housing 10' and insert 20' have a more compact shape and the geometry of their respective cross-sections is chosen such that they can be attached to a male part in the form of a round bar 30' as it is shown in FIG. 29.

As in the first exemplary embodiment, female housing 10' includes a series of adjoining basic housing elements having each a length L and into each of which an elastic insert 20' is insertable.

Figure 25:
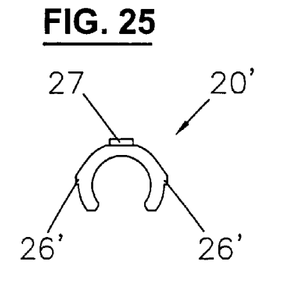
FIG. 25 shows a second exemplary embodiment of an insert of an arrangement according to the invention in a front view.
Figure 26:
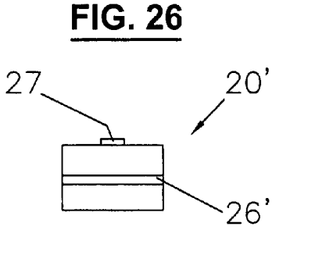
FIG. 26 shows the insert of FIG. 25 in a side view.
Figure 27:
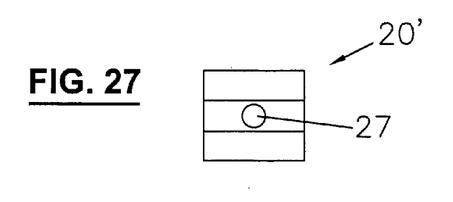
FIG. 27 shows the insert of FIG. 25 in a top view.
Figure 28:
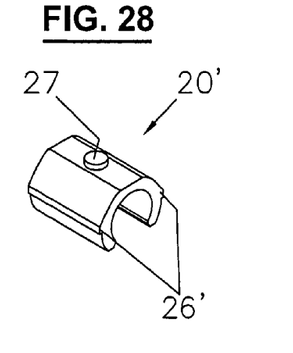
FIG. 28 shows the insert of FIG. 25 in a perspective view.

As appears particularly in FIG. 25, insert 20' is provided on each side with a step to form longitudinal wings 26' and on its occlusal side with projection 27. The inner surface of insert 20' has an essentially circular cross-section whose arc length is longer than half the circumference of the circle.

As appears particularly in the greatly enlarged illustration of FIG. 30, the two side walls 12' are shorter than side walls 12 of first female housing 10. Side walls 12' are each provided with a longitudinal groove 16'. The cross-section of longitudinal groove 16' is composed of three sections 16'*a*, 16'*b*, and 16'*c*, first section 16'*a* being essentially perpendicular to withdrawal direction 29, second section 16'*b* being essentially parallel to withdrawal direction 29, and third section 16'*c* being arranged at an angle α' with respect to second section 16'*b*. Angle α' is greater than 90 degrees and smaller than 180 degrees and is preferably comprised within a range of 125 degrees to 170 degrees. Sections 16'*a*, 16'*b*, and 16'*c* are substantially straight. As in the first exemplary embodiment, the shape of longitudinal groove 16' ensures that female housing 10' also resists high loads.

Figures 31, 32, 33, 34, 35:
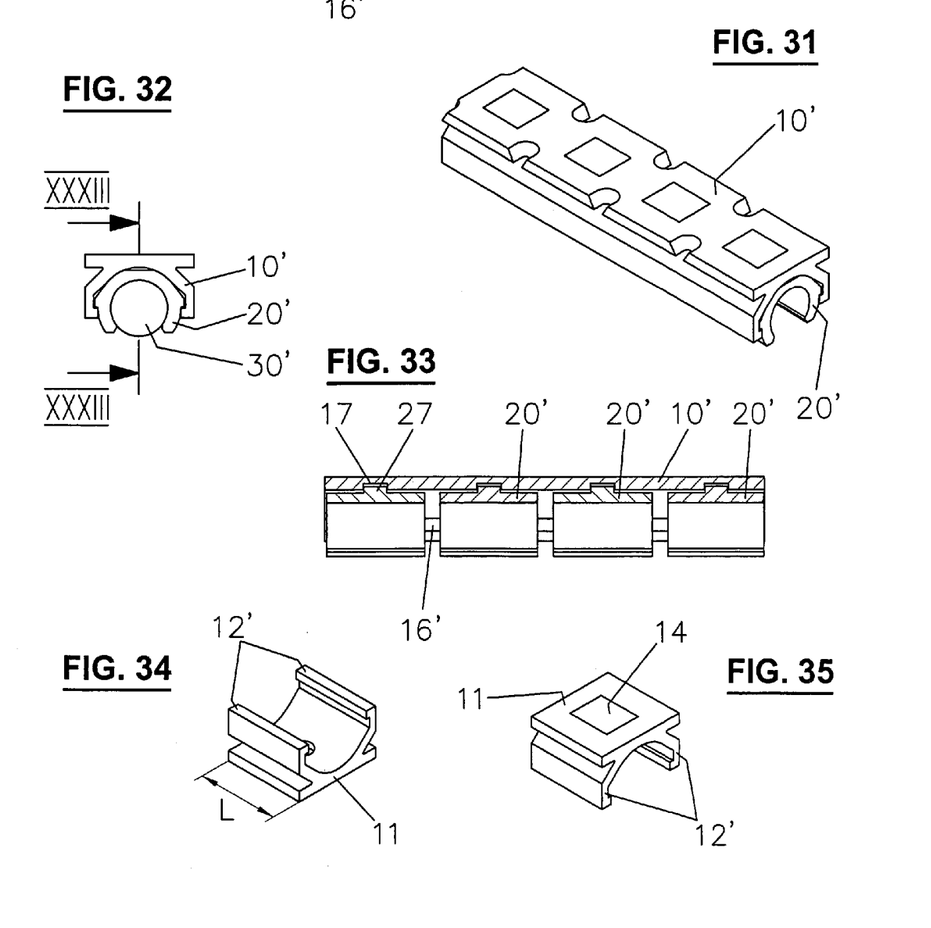
FIG. 31 shows the female housing of FIG. 20 with inserts according to FIG. 25 inserted therein in a perspective view from above.
FIG. 32 shows a front view of the arrangement of FIG. 31 attached to a male bar according to FIG. 29.
FIG. 33 shows the arrangement of FIG. 31 in a sectioned side view according to line XXXIII-XXXIII in FIG. 32, the male bar not being shown.
FIG. 34 shows the basic housing element of the female housing of FIG. 20 in a perspective view from below.
FIG. 35 shows the basic housing element of FIG. 34 in a perspective view from above.

As appears in FIGS. 31 to 33, longitudinal wings 26' of insert 20' engage in the respective longitudinal grooves 16' and projection 27 engages in recess 17.

In order to facilitate the insertion of insert 20' into female housing 10', the distance between section 16'*a* and the curved portion of female housing 10' is made a little larger than the corresponding dimension of insert 20'. This results in a clearance between female housing 10' and insert 20', which however disappears on account of the tension of insert 20' when the female housing is attached to male bar 30'.

As shown in FIG. 32, insert 20' extends over bar 30' and extends beyond the basal edge of female housing 10'. Female housing 10' is both frictional and retentive, i.e. it is retained on bar 30' combinedly by friction and by the chosen geometry.

The manufacture, the choice of materials, and the possible applications of female housing 10' and of insert 20' are the same as in the first exemplary embodiment.

Again, as shown in FIGS. 34 and 35, an individual female housing 10' may be provided that corresponds to the basic housing element and into which insert 20' is insertable.

Third Exemplary Embodiment

Figure 36:
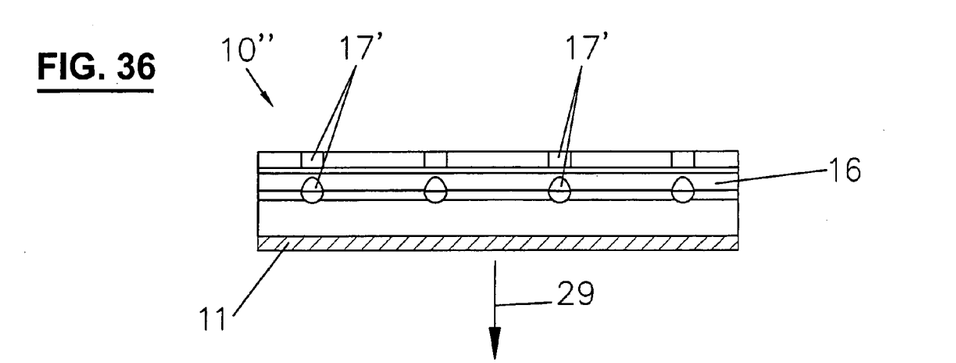
FIG. 36 shows a third exemplary embodiment of the female housing of an arrangement according to the invention in a sectioned side view according to line XXXVI-XXXVI in FIG. 37.
Figure 37:
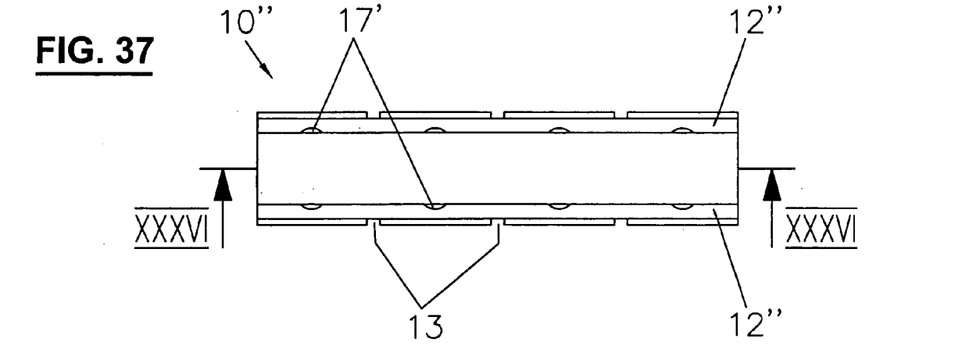
FIG. 37 shows the female housing of FIG. 36 in a bottom view.
Figure 38:
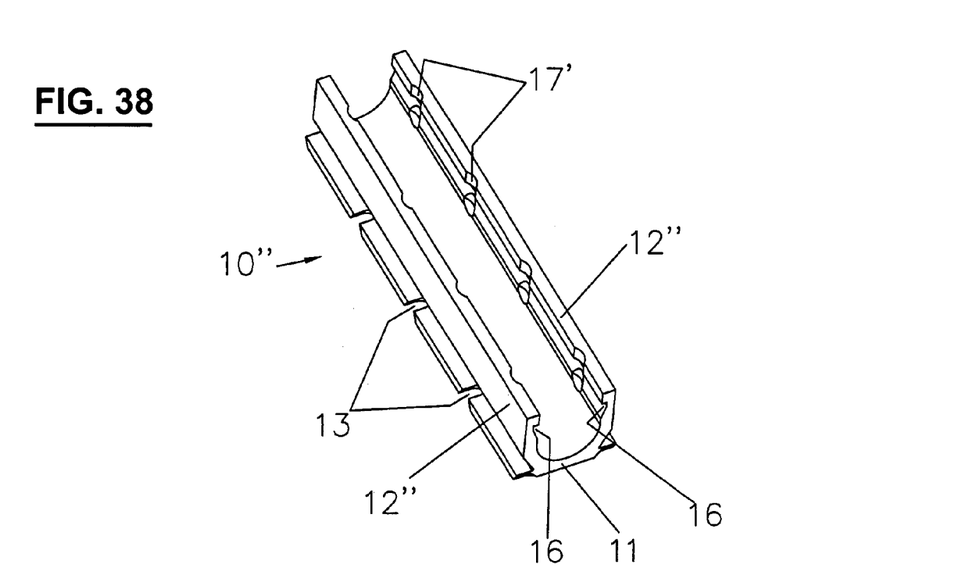
FIG. 38 shows the female housing of FIG. 36 in a perspective view from below.
Figure 39:
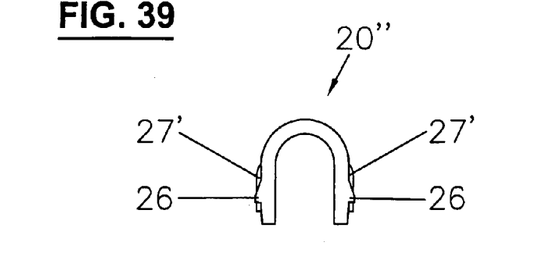
FIG. 39 shows a third exemplary embodiment of an insert of an arrangement according to the invention in a front view.
Figure 40:
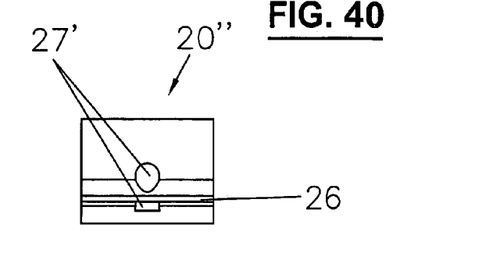
FIG. 40 shows the insert of FIG. 39 in a side view.
Figures 41, 42:
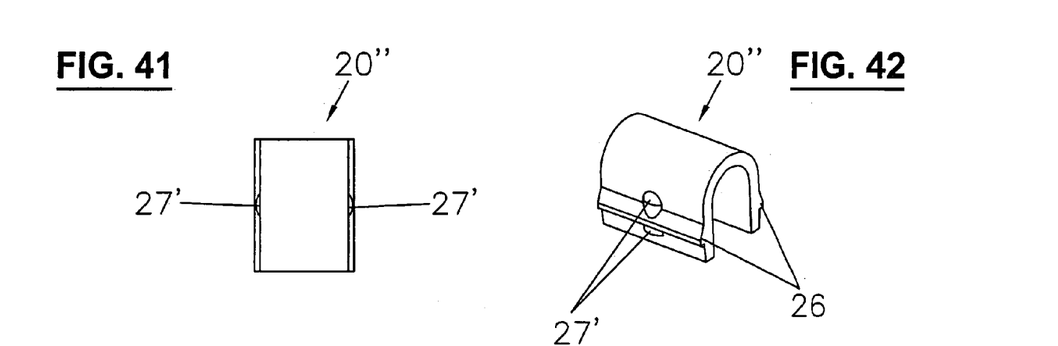
FIG. 41 shows the insert of FIG. 39 in a top view.
FIG. 42 shows the insert of FIG. 39 in a perspective view.

FIGS. 36 to 38 show a third exemplary embodiment of female housing 10" and FIGS. 39 to 42 show the appropriate insert 20". Parts that correspond to the parts of the first exemplary embodiment are designated by the same reference numerals.

The third exemplary embodiment is similar to the first exemplary embodiment and essentially differs therefrom in the design of positioning means 17', 27'.

As shown in FIGS. 36 to 38, female housing 10" has recesses 17' that are provided in the two side walls 12" of female housing 10" at regular spaces and extend essentially in the direction of withdrawal direction 29. Recesses 17' are formed by grooves extending from the basal end of female housing 10' toward cover plate 11. In the embodiment represented here, recesses 17' cross longitudinal grooves 16.

As shown in FIGS. 39 to 42, insert 20" is provided on both of its external longitudinal sides with respective projections 27' extending in the withdrawal direction. In the embodiment represented here, projections 27' cross longitudinal wings 26.

Figure 43:
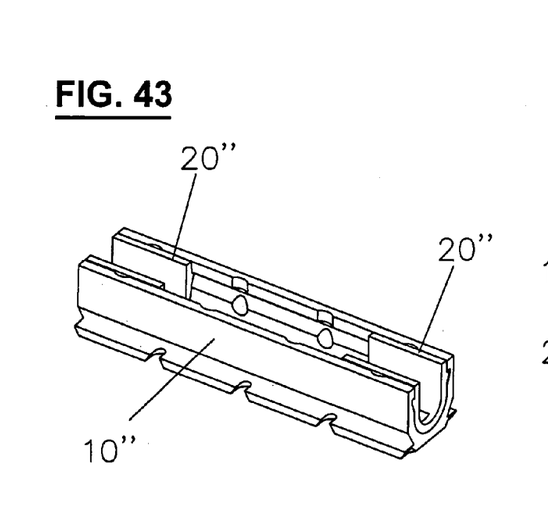
FIG. 43 shows the female housing of FIG. 36 with two inserts according to FIG. 39 inserted therein in a perspective view from below.
Figure 44:
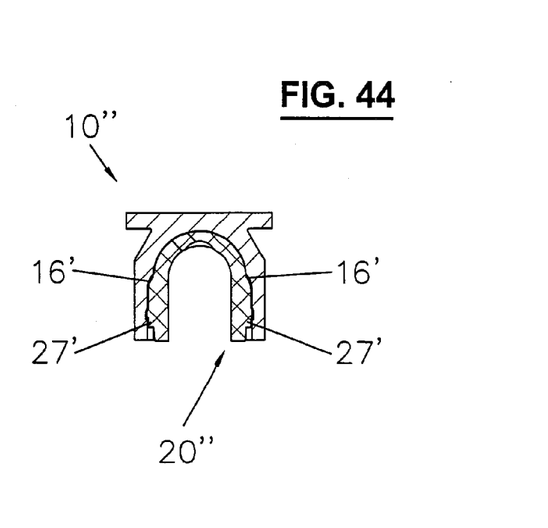
FIG. 44 shows a sectioned front view of the arrangement according to FIG. 43.

When insert 20" is inserted into female housing 10", each projection 27' engages in a respective recess 17' of female housing 10", as appears in FIGS. 43 and 44.

Arranging recesses 17' in side walls 12" of female housing 10" offers the advantage that a user can clearly see recesses 17' and easily insert an insert 20" at the desired position of female housing 10". Furthermore, insert 20" is safely maintained in its position inside female housing 10" by means of positioning means 17', 27'.

As appears in FIG. 44 in particular, projections 27' do not extend up to the basal end of female housing 10". Therefore, a space that is accessible from the outside remains between female housing 10" and insert 20". A suitable tool can be engaged in this space and insert 20" is thus easily removed from female housing 10".

Fourth Exemplary Embodiment

Figure 45:
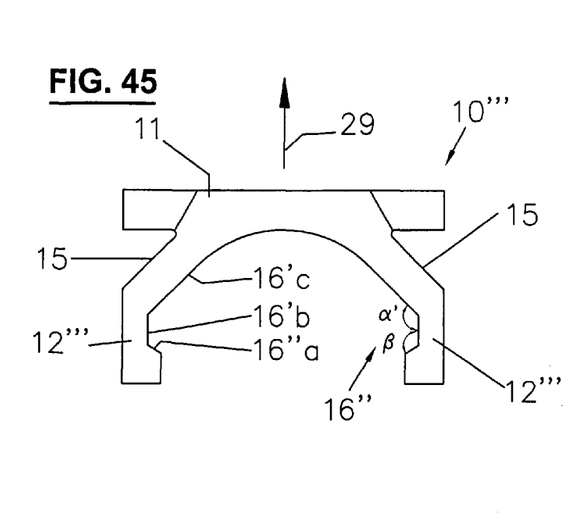
FIG. 45 shows a fourth exemplary embodiment of the female housing of an arrangement according to the invention in a front view.

FIG. 45 shows a fourth exemplary embodiment of female housing 10''' and FIGS. 46 to 50 show the appropriate insert 20'''. Parts that correspond to the parts of the first exemplary embodiment are designated by the same reference numerals.

The fourth exemplary embodiment is similar to the second exemplary embodiment and essentially differs therefrom in the design of longitudinal grooves 16", longitudinal wings 26", and positioning means 17', 27'.

As seen in FIG. 45, the cross-section of longitudinal groove 16' is composed of three sections 16"a, 16'b, and 16'c. In contrast to the second exemplary embodiment, first section 16"a is slightly inclined rather than perpendicular to withdrawal direction 29. Sections 16"a and 16'b are therefore arranged at an angle β that is greater than 90 degrees and smaller than 180 degrees and is preferably comprised in the range of 110 degrees to 160 degrees, e.g. at 120 degrees.

Figure 46:
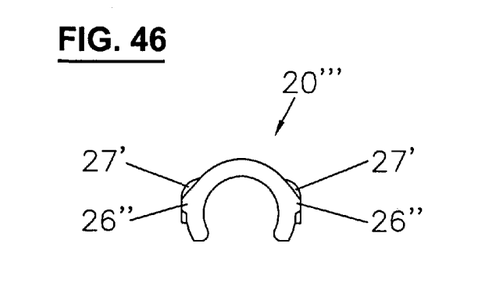
FIG. 46 shows a fourth exemplary embodiment of an insert of an arrangement according to the invention in a front view.
Figure 47:
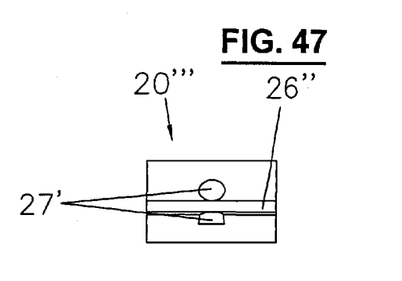
FIG. 47 shows the insert of FIG. 46 in a side view.
Figure 48:
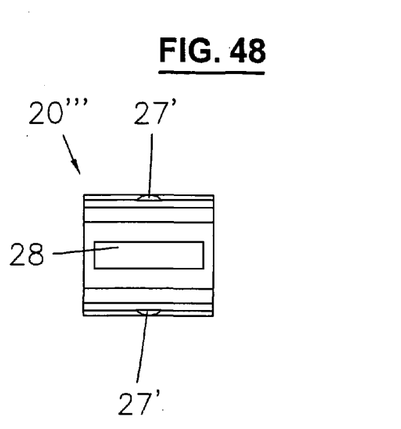
FIG. 48 shows the insert of FIG. 46 in a bottom view.
Figure 49:
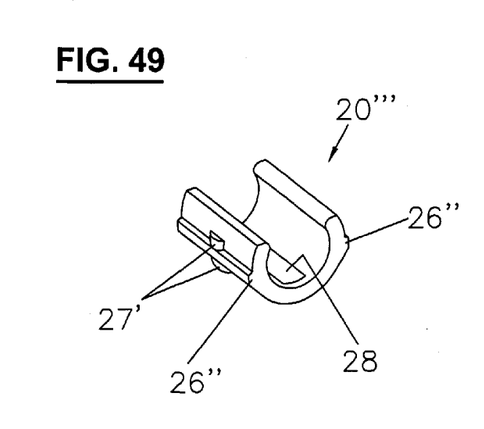
FIG. 49 shows the insert of FIG. 46 in a perspective view from below.
Figure 50:
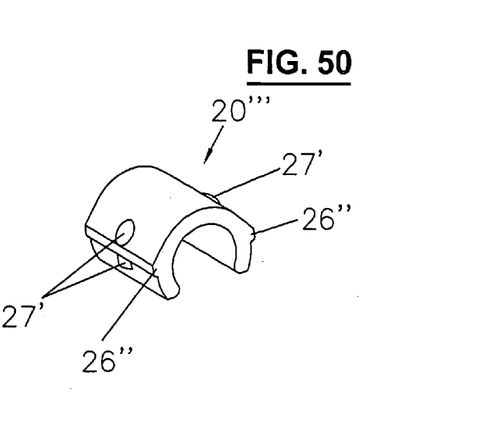
FIG. 50 shows the insert of FIG. 46 in a perspective view from above.
Figure 51:
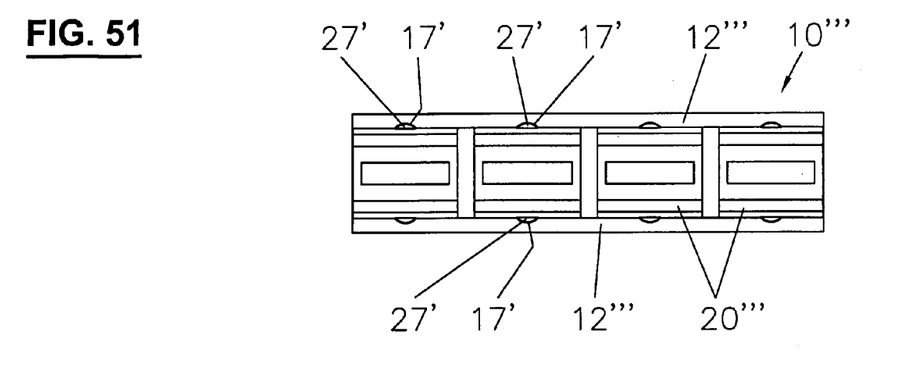
FIG. 51 shows the female housing of FIG. 45 with four inserts according to FIG. 46 inserted therein in a bottom view.
Figure 52:
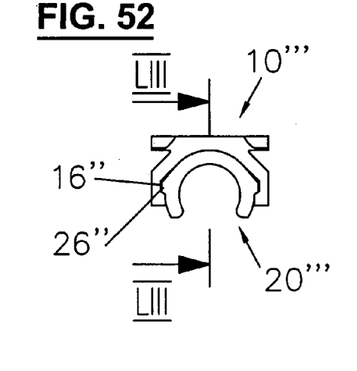
FIG. 52 shows a front view of the arrangement according to FIG. 51.
Figure 53:
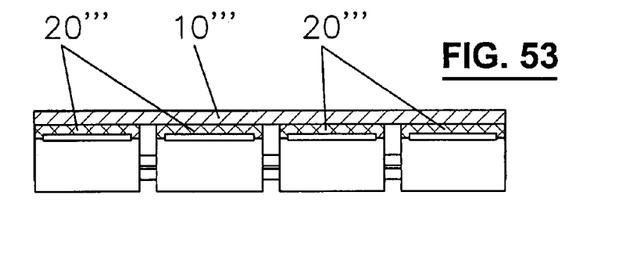
FIG. 53 shows a side view of the arrangement according to FIG. 51 in a sectional view according to line LIII-LIII in FIG. 52.
Figure 54:
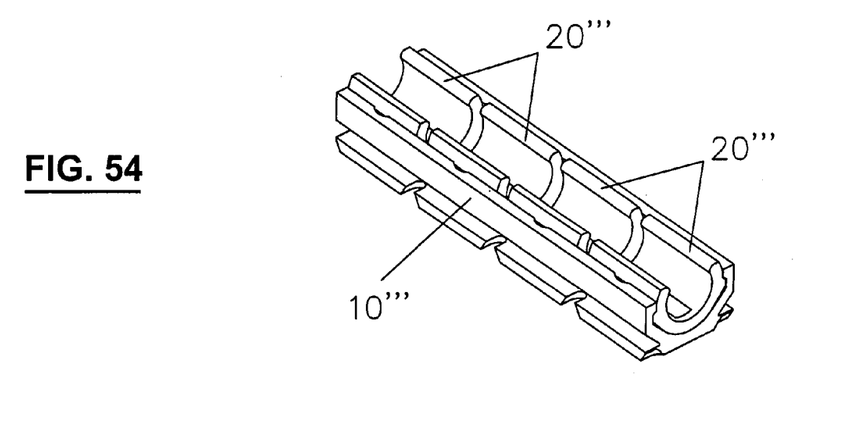
FIG. 54 shows a perspective view of the arrangement according to FIG. 51 seen from below.

As shown in FIG. 46, longitudinal wings 26" of insert 20''' each have a chamfered underside. The latter comes to rest on section 16"a when insert 20''' is inserted in female housing 10''' (see FIG. 52). The inclined arrangement of section 16"a and of longitudinal wing 26" facilitates the insertion of insert 20''' into female housing 10'''.

As shown in FIGS. 46 to 50, insert 20''' is provided on both of its external longitudinal sides with respective projections 27' of the kind described in the third exemplary embodiment.

Insert 20''' is internally provided with a recess 28. If an auxiliary tool is to be used for inserting insert 20''' into female housing 10''', recess 28 allows a precise grasp of insert 20''' by means of the auxiliary tool.

To allow insert 20''' to be introduced into female housing 10''' at the desired position and maintained therein, the latter is provided in both side walls 12''' with recesses 17' as described with reference to the third exemplary embodiment. In FIGS. 51 to 54, an example of a female housing 10''' is shown in which four inserts 10''' are inserted. As appears in the figures, the respective projections 27' and longitudinal wings 26" engage in recesses 17' and longitudinal grooves 16", respectively.

The exemplary embodiments described thus far offer the following advantages, amongst others:

The retention force and withdrawal force can be adjusted in various ways by selectively providing the basic housing element with an insert or leaving it unoccupied.

The same insert can be inserted into each basic housing element of the female housing and subsequently removed therefrom, if necessary. If the female housing is shortened, the same insert can still be used without requiring any modification.

The female housing can be prefabricated by means of a machine so that a dental prosthesis can be provided with means for its attachment to a male bar in a relatively simple and inexpensive manner. The female housing is simply adaptable to the given geometric situation by being shortened.

By arranging incisions in the female housing, means that define positions for shortening the female housing by means of a cutting-off wheel and that serve for guiding the cutting-off wheel in the cutting operation can be provided in a simple manner.

Providing insert 20, 20', 20", 20''' with at least one projection 27, 27' in order to position it inside a female housing 10, 10', 10", 10''' and secure it against a longitudinal displacement is a measure that is also applicable in other female housings, e.g. housings that are cast by the dental technician. To this end, an insert 20, 20', 20", 20''' is directly attached to bar 30, 30' in order to prepare a duplicate thereof. On this duplicate, wax modelation for model casting is performed. The cast model or the cast female housing, respectively, is thus provided with a recess 17, 17' in which projection 27, 27' of insert 20, 20', 20", 20''' inserted therein engages, thereby precisely positioning and securing the latter against any displacement.

The cross-sectional geometry of female housing 10, 10', 10", 10''' and of insert 20, 20', 20", 20''' may be adapted to all male bars of the prior art, e.g. bars having a cross-section with parallel walls or a round, oval, egg-shaped one, etc. Accordingly, the female housing and the bar together either form a bar joint where the female housing is allowed to rotate about the bar axis or a bar attachment where the female housing is rigidly connected to the bar.

Of course, the holding mechanism by means of longitudinal groove 16, 16' and longitudinal wing 26, 26', 26" can also be realized by providing female housing 10, 10', 10", 10''' with longitudinal wings 26, 26', 26" and insert 20, 20', 20", 20''' with longitudinal grooves 16, 16', 16''. Likewise, positioning means 17, 27 or 17', 27' may have a complementary configuration where female housing 10, 10', 10'', 10''' is provided at essentially regular spaces with projections that may engage in recesses in the respective inserts 20, 20', 20'', 20'''.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An arrangement for fastening a dental prosthesis to a male bar, comprising:
    a female housing that is connectable to said dental prosthesis; and
    at least two separate inserts configured to adjust a retention force retaining said female housing on said male bar, each of said at least two separate inserts being insertable into said female housing in a removable way and having a channel extending from a first lateral end to a second lateral end, said first lateral end with a first opening and said second lateral end with a second opening, said first opening and said second opening being arranged opposite to each other such that said male bar extends through said first opening and said second opening when one of the at least two inserts is inserted in said female housing and said female housing is attached to said male bar,
    wherein said female housing and said at least two inserts comprise positioning elements for determining a position of said at least two inserts inside said female housing.

2. The arrangement according to claim 1, wherein said female housing is made in one piece and comprises a number of adjoining, essentially identical basic housing elements, said at least two inserts being insertable into every one of said basic housing elements.

3. The arrangement according to claim 1, wherein outer surfaces of the female housing extend in a substantially straight direction.

4. The arrangement according to claim 1, wherein said positioning elements of said female housing are arranged on said female housing at substantially regular spaces.

5. The arrangement according to claim 1, wherein said positioning elements comprise recesses and projections, at least one of said projections engaging in one of said recesses when one of said at least two inserts has been inserted into said female housing.

6. The arrangement according to claim 1, wherein the length of said at least two inserts is chosen such that a space is formed when two of said at least two inserts are inserted in two neighboring positions of said female housing.

7. The arrangement according to claim 1, wherein said female housing is provided with marks that are arranged at substantially regular spaces.

8. The arrangement according to claim 7, wherein said marks are at least one of the following: incisions, grooves, and engravings.

9. The arrangement according to claim 1,
    wherein said female housing has incisions that define positions for shortening said female housing by a cutting-off wheel and that serve for guiding said cutting-off wheel during a cutting operation.

10. The arrangement according to claim 1, wherein said at least two inserts includes a synthetic material.

11. The arrangement according to claim 10, wherein said synthetic material is polyetheretherketone (PEEK) or polyoxymethylene (POM).

12. The arrangement according to claim 1, wherein said female housing includes a synthetic material.

13. The arrangement according to claim 12, wherein said synthetic material is polyetheretherketone (PEEK) or polyoxymethylene (POM).

14. The arrangement according to claim 1,
    wherein said female housing has at least two longitudinal grooves and each of said at least two inserts has longitudinal wings for engaging in said longitudinal grooves.

15. The arrangement according to claim 1, further comprising an auxiliary part for casting said female housing, for shortening said female housing, or for a combination thereof, said auxiliary part corresponding essentially to the shape of at least one of said at least two inserts and having essentially the same size or an overdimensioned size of said at least two inserts.

16. The arrangement according to claim 1, wherein each of said at least two inserts includes a substantially U-shaped cross-section.

17. An arrangement for fastening a dental prosthesis to a male bar, comprising:
    a female housing that is connectable to said dental prosthesis; and
    at least two separate inserts configured to adjust a retention force retaining said female housing on said male bar, each of said at least two separate inserts being insertable into said female housing in a removable way and having lateral end with openings through which said male bar extends when one of the at least two inserts is inserted in said female housing and said female housing is attached to said male bar,
    wherein said female housing and said at least two inserts comprise positioning elements for determining a position of said at least two inserts inside said female housing,
    wherein said female housing has at least two longitudinal grooves and each of said at least two inserts has longitudinal wings for engaging in said longitudinal grooves, and
    wherein said female housing being attached to said male bar is removable in a withdrawal direction, the cross-section of each said longitudinal grooves comprising:
        a first section,
        a second section that is closer to an occlusal side of said female housing than said first section and is essentially parallel to said withdrawal direction, wherein the first section adjoins to the second section, and
        a third section, wherein the second section adjoins to the third section,
        wherein the angle between said second section and said third section is in a range between 90 degrees and 180 degrees.

18. The arrangement according to claim 17, wherein said angle is in a range between 125 degrees and 170 degrees.

* * * * *

UNITED STATES PATENT AND TRADEMARK OFFICE
CERTIFICATE OF CORRECTION

| | | |
|---|---|---|
| PATENT NO. | : 8,092,218 B2 | Page 1 of 1 |
| APPLICATION NO. | : 11/812494 | |
| DATED | : January 10, 2012 | |
| INVENTOR(S) | : Adrian Auderset et al. | |

It is certified that error appears in the above-identified patent and that said Letters Patent is hereby corrected as shown below:

ON THE COVER PAGE OF THE PATENT:

Item (73), should read: -- Assignee: Cendres & Métaux SA, Biel/Bienne (CH) --.

IN THE CLAIMS:

Claim 17, col. 10, line 36, "lateral end" should be -- lateral ends --.

Signed and Sealed this
Twenty-ninth Day of May, 2012

David J. Kappos
*Director of the United States Patent and Trademark Office*